(12) United States Patent
Snell et al.

(10) Patent No.: US 10,669,217 B2
(45) Date of Patent: Jun. 2, 2020

(54) WAYS TO PREVENT PUMP-AROUND HEAT EXCHANGER FOULING AND EXTEND RUN LENGTHS ON A BENZENE HYDROGENATION UNIT

(71) Applicant: Chevron Phillips Chemical Company LP, The Woodlands, TX (US)

(72) Inventors: Ryan W. Snell, Jubail Industrial (SA); Israel Garcia, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 16/555,170

(22) Filed: Aug. 29, 2019

(65) Prior Publication Data
US 2019/0382322 A1 Dec. 19, 2019

Related U.S. Application Data

(62) Division of application No. 15/899,200, filed on Feb. 19, 2018, now abandoned.

(51) Int. Cl.
*C07C 5/10* (2006.01)
*B01J 19/24* (2006.01)

(52) U.S. Cl.
CPC ............ *C07C 5/10* (2013.01); *B01J 19/2465* (2013.01); *B01J 2219/00103* (2013.01); *B01J 2219/24* (2013.01); *C07C 2523/755* (2013.01); *C07C 2531/14* (2013.01)

(58) Field of Classification Search
CPC ....................................................... C07C 5/10
USPC .................................................. 585/270, 269
See application file for complete search history.

(56) References Cited

U.S. PATENT DOCUMENTS

| | | | |
|---|---|---|---|
| 3,505,421 A | 4/1970 | Lumbroso et al. | |
| 3,597,489 A | 8/1971 | Vu et al. | |
| 3,621,068 A | 11/1971 | Jacques et al. | |
| 4,357,478 A | 11/1982 | Hillion et al. | |
| 5,668,293 A | 9/1997 | Forestiere et al. | |
| 5,670,437 A | 9/1997 | Durand et al. | |
| 2008/0004476 A1 | 1/2008 | Himelfarb et al. | |

*Primary Examiner* — Thuan D Dang
(74) *Attorney, Agent, or Firm* — Conley Rose, P.C.

(57) ABSTRACT

A process for hydrogenation of an aromatic hydrocarbon including introducing a hydrocarbon feed comprising the aromatic hydrocarbon, a hydrogen feed comprising hydrogen, and a hydrogenation catalyst into a hydrogenation reactor operable with a liquid phase and a gas phase to produce a hydrogenation product; removing a gas phase product stream comprising the hydrogenation product; withdrawing a portion of the liquid phase; subjecting the withdrawn portion to heat exchange to provide a reduced-temperature withdrawn portion; introducing the reduced-temperature withdrawn portion back into the hydrogenation reactor; and at least one of: (a) providing at least two heat exchangers to effect the subjecting of the withdrawn portion of the liquid phase to heat exchange; (b) separating a decomposition product of the hydrogenation catalyst, the hydrogenation catalyst, or both, from the withdrawn portion of the liquid phase prior to the heat exchange; and (c) reducing exposure of the hydrogenation catalyst to an oxygen-containing species.

21 Claims, 2 Drawing Sheets

WAYS TO PREVENT PUMP-AROUND HEAT EXCHANGER FOULING AND EXTEND RUN LENGTHS ON A BENZENE HYDROGENATION UNIT

CROSS-REFERENCE TO RELATED APPLICATIONS

This application is a divisional of and claims priority to U.S. patent application Ser. No. 15/899,200 filed on Feb. 19, 2018, published as U.S. Patent Application Publication No. 2019/0256443 A1 and entitled "Ways to Prevent Pump-Around Heat Exchanger Fouling and Extend Run Lengths on a Benzene Hydrogenation Unit," which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This disclosure relates to the hydrogenation of aromatic hydrocarbons; still more specifically, this disclosure relates to a system and method for liquid phase hydrogenation of aromatic hydrocarbons; even more specifically, this disclosure relates to the liquid phase hydrogenation of benzene to produce cyclohexane.

BACKGROUND

Cyclohexane is currently produced using a liquid phase benzene hydrogenation reactor. As the hydrogenation reaction is quite exothermic, heat must be continuously removed from the system. Heat removal is primarily effected via a pump-around loop, via which withdrawn reactor liquid phase is continuously moved through a heat exchanger in which it is cooled. The heat exchanger often operates to produce low pressure steam. The cooled liquid is returned to the hydrogenation reactor. Fresh catalyst may be added to this cooled liquid prior to reintroduction into the hydrogenation reactor.

Undesirably, the catalyst may gradually plate out on the heat exchanger, resulting in reduced performance of the heat exchanger, and eventually a need to shut the plant down. The decrease in run life and concomitant increase in the number of turnarounds is uneconomical and detrimental to the overall unit economics.

An ongoing need thus exists for a system and process that reduce or eliminate heat exchanger fouling during the hydrogenation of aromatic hydrocarbon(s), and/or allow for cleaning of the heat exchanger without halting production.

SUMMARY

Disclosed herein is a process for liquid phase hydrogenation of an aromatic hydrocarbon, the process comprising: introducing a hydrocarbon feed comprising the aromatic hydrocarbon, a hydrogen feed comprising hydrogen, and a hydrogenation catalyst into a hydrogenation reactor operable with a liquid phase and a gas phase, whereby at least a portion of the aromatic hydrocarbon is hydrogenated to produce a hydrogenation product; removing, from the hydrogenation reactor, a gas phase product stream comprising the hydrogenation product; withdrawing, from the hydrogenation reactor, a portion of the liquid phase; subjecting at least a portion of the withdrawn portion of the liquid phase to heat exchange, thus providing a reduced-temperature withdrawn portion; introducing the reduced-temperature withdrawn portion back into the hydrogenation reactor; and at least one of: (a) providing at least two heat exchangers to effect the subjecting of the withdrawn portion of the liquid phase to heat exchange, such that a first heat exchanger of the at least two heat exchangers can be online while a second heat exchanger of the at least two heat exchangers is offline; (b) separating a decomposition product of the hydrogenation catalyst, the hydrogenation catalyst, or both, from the withdrawn portion of the liquid phase prior to subjecting the at least a portion of the withdrawn portion of the liquid phase to heat exchange; and (c) reducing exposure of the hydrogenation catalyst to an oxygen-containing species.

Also disclosed herein is a system for liquid phase hydrogenation, the system comprising: a hydrogenation reactor operable with a liquid phase and a gas phase to convert an aromatic hydrocarbon in a hydrocarbon feed to a hydrogenation product by contacting the aromatic hydrocarbon with hydrogen in a hydrogen feed in the presence of a hydrogenation catalyst; a pump-around loop comprising a pump configured to move a withdrawn portion of the liquid phase from the hydrogenation reactor through the pump-around loop and back to the hydrogenation reactor; at least one primary heat exchanger after the pump in the pump-around loop and configured to reduce the temperature of at least a portion of the liquid phase withdrawn from the hydrogenation reactor, thus providing a reduced-temperature withdrawn portion, prior to introduction of the reduced-temperature withdrawn portion into the hydrogenation reactor; and at least one of: (a) at least one additional heat exchanger in parallel with the at least one primary heat exchanger, and configured such that the at least one primary heat exchanger can be placed offline while the at least one additional heat exchanger is placed online; (b) a separator upstream of the at least one primary heat exchanger, and configured to separate a decomposition product of the hydrogenation catalyst, the hydrogenation catalyst, or both from the withdrawn portion of the liquid phase; and (c) a dryer operable to dry the hydrocarbon feed, the hydrogen feed, both the hydrocarbon feed and the hydrogen feed, or a mixture of the hydrocarbon feed and the hydrogen feed; a source of a component that will react with an oxygen-containing species in the hydrocarbon feed, the hydrogen feed, or both; or both the dryer and the source of the component.

Also disclosed herein is a process for hydrogenation of benzene to cyclohexane, the process comprising: introducing a benzene feed comprising benzene, a hydrogen feed comprising hydrogen, and a hydrogenation catalyst comprising nickel into a hydrogenation reactor operable with a liquid phase and a gas phase, whereby at least a portion of the benzene is hydrogenated to produce cyclohexane; removing from the hydrogenation reactor a gas phase product stream comprising cyclohexane; withdrawing from the liquid phase a pump-around stream from the reactor; passing at least a portion of the pump-around stream to a heat exchanger bank comprising at least a first heat exchanger in parallel with a second heat exchanger such that the first heat exchanger can be online while the second heat exchanger is offline, and vice versa; cooling the at least a portion of the pump-around stream in the heat exchanger bank to provide a reduced-temperature pump-around stream; and introducing the reduced-temperature pump-around stream back into the hydrogenation reactor.

Also disclosed herein is a process for hydrogenation of benzene to cyclohexane, the process comprising: introducing a benzene feed comprising benzene, a hydrogen feed comprising hydrogen, and a hydrogenation catalyst slurry comprising a supported nickel catalyst into a hydrogenation reactor operable with a liquid phase and a gas phase, whereby at least a portion of the benzene is hydrogenated to produce cyclohexane; removing a product stream comprising cyclohexane from the gas phase of the hydrogenation reactor; withdrawing a pump-around stream from the liquid phase of the hydrogenation reactor, wherein the pump-around stream comprises supported nickel catalyst; separating the supported nickel catalyst from the pump-around stream to produce a supported nickel catalyst stream and a substantially catalyst-free pump-around stream; passing at least a portion of the substantially catalyst-free pump-around stream to a heat exchanger; cooling the at least a portion of the substantially catalyst-free pump-around stream in the heat exchanger to provide a reduced-temperature pump-around stream; and introducing the reduced-temperature pump-around stream and at least a portion of the supported nickel catalyst stream back into the hydrogenation reactor.

Also disclosed herein is a process for hydrogenation of benzene to cyclohexane, the process comprising: treating a benzene feed comprising benzene to form a treated benzene feed, treating a hydrogen feed comprising hydrogen to form a treated hydrogen feed, both treating a benzene feed comprising benzene to form a treated benzene feed and treating a hydrogen feed comprising hydrogen to form a treated hydrogen feed, or treating a mixed feed comprising benzene and hydrogen to form a treated mixed feed, wherein treating reduces an amount of oxygen-containing species therein, wherein the oxygen containing species comprise carbon monoxide, carbon dioxide, oxygen, water, or a combination thereof; introducing the treated benzene feed, the treated hydrogen feed, both the treated benzene feed and the treated hydrogen feed, or the treated mixed feed, and a hydrogenation catalyst comprising nickel and at least one aluminum alkyl into a hydrogenation reactor operable with a liquid phase and a gas phase, whereby at least a portion of the benzene is hydrogenated to produce cyclohexane; removing a product stream comprising cyclohexane from the gas phase of the hydrogenation reactor; withdrawing a pump-around stream from the liquid phase of the hydrogenation reactor; passing at least a portion of the liquid phase pump-around stream to a heat exchanger; cooling the at least a portion of the liquid phase pump-around stream in the heat exchanger to provide a reduced-temperature pump-around stream, and introducing the reduced-temperature pump-around stream back into the hydrogenation reactor.

BRIEF DESCRIPTION OF THE DRAWINGS

The detailed description will reference the drawings briefly described below, wherein like reference numerals represent like parts, unless otherwise indicated.

DETAILED DESCRIPTION

Herein disclosed are systems and methods for hydrogenation of aromatic hydrocarbon(s). Although described with reference to the hydrogenation of benzene to produce cyclohexane, it is to be understood that the herein-disclosed system and method are likewise suitable for the hydrogenation of other aromatic hydrocarbons as well. The disclosed system and method provide for increased run length by reducing or substantially preventing the deposition of catalyst and/or catalyst decomposition products on a pump-around heat exchanger, and/or enabling continuous operation during cleaning of a pump around heat exchanger. Such systems and methods may thus provide for enhanced run lengths, and the concomitant savings on turnarounds.

The herein-disclosed system and process may enable or comprise introducing a hydrocarbon feed comprising the aromatic hydrocarbon, a hydrogen feed comprising hydrogen, and a hydrogenation catalyst into a hydrogenation reactor operable with a liquid phase and a gas phase, whereby at least a portion of the aromatic hydrocarbon is hydrogenated to produce a hydrogenation product; removing a gas phase product stream comprising the hydrogenation product from the hydrogenation reactor; withdrawing a portion of the liquid phase, subjecting at least a portion of the withdrawn portion of the reactor liquid phase to heat exchange, thus providing a reduced-temperature withdrawn portion, introducing the reduced-temperature withdrawn portion back into the hydrogenation reactor; and at least one of: (a) providing at least two heat exchangers to effect the subjecting of the withdrawn portion of the liquid phase to heat exchange, such that a first heat exchanger of the at least two heat exchangers can be online while a second heat exchanger of the at least two heat exchangers is offline; (b) separating a decomposition product of the hydrogenation catalyst, the hydrogenation catalyst, or both, from the withdrawn portion of the liquid phase prior to subjecting the at least a portion of the withdrawn portion of the liquid phase to heat exchange; (c) reducing exposure of the hydrogenation catalyst to an oxygen-containing species; or (d) combinations thereof.

In embodiments, shut-down of the hydrogenation unit is made unnecessary by adding a second heat exchanger, according to (a), which may be utilized while the other heat exchanger is being cleaned, such that the hydrogenation unit remains operating during the cleaning. In embodiments, the first (or primary) heat exchanger and the second heat exchanger are substantially identical. In embodiments, the second heat exchanger is smaller than the first or primary heat exchanger. The first heat exchanger and the second heat exchanger may operate with cooling media having different compositions, may operate with different inlet temperatures, or both. In embodiments, the cooling medium of the first or primary heat exchanger is boiler feed water and low pressure steam is produced therein, and the cooling medium of the second heat exchanger is selected from the group consisting of cooling water and refrigerants.

In embodiments, catalyst deposition on the heat exchanger is prevented or minimized via (b). In such embodiments, solid decomposition products of the hydrogenation catalyst, or a solid hydrogenation catalyst, or both, may be separated prior to the heat exchange. In some such embodiments, a supported catalyst is employed, with the hydrogenation being operated as a slurry, and the supported catalyst is separated from the withdrawn liquid phase upstream or downstream of a pump of the pump-around loop, whereby solids can be removed upstream of the heat exchanger. In embodiments, separating hydrogenation catalyst and/or decomposition product thereof from the withdrawn portion of the liquid phase comprises introducing the withdrawn portion of the liquid phase into a cyclone. The withdrawn portion of the liquid phase may be pumped into at least one heat exchanger via a pump, and the cyclone may be upstream of the pump or it may be downstream of the pump. At least a portion of the separated hydrogenation catalyst can be reintroduced into the hydrogenation reactor. At least a portion of the separated hydrogenation catalyst and/or of the separated decomposition product of the hydrogenation catalyst may be purged. In embodiments, the hydrogenation catalyst further comprises a support. In embodiments, the support comprises at least one component selected from the group consisting of silica, alumina, and carbon.

In embodiments, run length may be increased by (c), by selectively removing oxygen-containing species, such as, without limitation, carbon monoxide, carbon dioxide, oxygen, and water, from the feed and/or from the hydrogenation reactor. Selectively removing oxygen-containing species may comprise drying the hydrocarbon feed, the hydrogen feed, or both (i.e., drying both the hydrogen feed and the hydrocarbon feed separately, or drying a mixed feed containing both the hydrocarbon feed and the hydrogen feed) prior to introducing same into the hydrogenation reactor, and/or adding a component to the hydrocarbon feed, the hydrogen feed, or both (i.e., adding the component to both the hydrogen feed and the hydrocarbon feed separately, or adding the component to a mixed feed containing both the hydrocarbon feed and the hydrogen feed), wherein the component is a compound that will react with the oxygen-containing species. The compound may be selected from the group consisting of aluminum alkyls. In embodiments, the hydrocarbon feed and the hydrogen feed are combined to provide a combined or mixed feed prior to introducing the combined or mixed feed into the hydrogenation reactor. In such embodiments, adding a component to the hydrocarbon feed, the hydrogen feed, or both may comprise adding the component to the combined or mixed feed.

In embodiments, hydrogenation of an aromatic hydrocarbon is effected via at least one step selected from the group consisting of (a) providing at least two heat exchangers to effect the subjecting of the withdrawn portion of the liquid phase to heat exchange, (b) separating the hydrogenation catalyst, a decomposition product of the hydrogenation catalyst, or both, from the withdrawn portion of the liquid phase prior to subjecting the withdrawn portion of the liquid phase to heat exchange, and (c) reducing exposure of the hydrogenation catalyst to an oxygen-containing species.

In embodiments, hydrogenation of an aromatic hydrocarbon is effected via a combination of two or more steps selected from the group consisting of (a) providing at least two heat exchangers to effect the subjecting of the withdrawn portion of the liquid phase to heat exchange, (b) separating the hydrogenation catalyst, a decomposition product of the hydrogenation catalyst, or both, from the withdrawn portion of the liquid phase prior to subjecting the withdrawn portion of the liquid phase to heat exchange, and (c) reducing exposure of the hydrogenation catalyst to an oxygen-containing species.

Herein disclosed is a system operable for the hydrogenation of aromatic hydrocarbon(s). A system for liquid phase hydrogenation according to this disclosure comprises a hydrogenation reactor operable with a liquid phase and a gas phase to convert an aromatic hydrocarbon in a hydrocarbon feed to a hydrogenation product by contacting the aromatic hydrocarbon with hydrogen in a hydrogen feed in the presence of a hydrogenation catalyst; a pump-around loop comprising a pump configured to move a withdrawn portion of the liquid phase from the hydrogenation reactor through the pump-around loop and back to the hydrogenation reactor; at least one primary heat exchanger after the pump in the pump-around loop and configured to reduce the temperature of at least a portion of the liquid phase withdrawn from the hydrogenation reactor, thus providing a reduced-temperature withdrawn portion, prior to introduction of the reduced-temperature withdrawn portion back into the hydrogenation reactor; and at least one of: (a) at least one additional heat exchanger in parallel with the at least one primary heat exchanger, and configured such that the at least one primary heat exchanger can be placed offline while the at least one additional heat exchanger is placed online; (b) a separator upstream of the at least one primary heat exchanger, and configured to separate the hydrogenation catalyst, a decomposition product of the hydrogenation catalyst, or both, from the withdrawn portion of the liquid phase; (c) a dryer operable to dry the hydrocarbon feed, the hydrogen feed, both the hydrocarbon feed and the hydrogen feed, or a mixture of the hydrocarbon feed and the hydrogen feed; a source of a component that will react with an oxygen-containing species in the hydrocarbon feed, the hydrogen feed, or both; or both the dryer and the source of the component; or (d) combinations thereof.

In embodiments, therefore, a hydrogenation system of this disclosure comprises (a), at least one additional heat exchanger in parallel with the at least one primary heat exchanger, and configured such that the at least one primary heat exchanger can be placed offline while the at least one additional heat exchanger is placed online. Description of such a hydrogenation system will now be made with reference to FIG. 1, which is a schematic of a hydrogenation system 100, according to an embodiment of this disclosure, which utilizes two substantially equal heat exchangers. Hydrogenation system 100 comprises hydrogenation reactor 120, pump 130, first (or 'primary') heat exchanger 140A, and second (or 'additional) heat exchanger 140B. Liquid phase hydrogenation system 100 is operable such that first heat exchanger 140A can be placed online while second heat exchanger 140B can be placed offline, and vice versa. Via this arrangement, hydrogenation reactor 120 can be kept online while one of the heat exchangers 140A/B is cleaned or serviced, by placing the other of the heat exchangers 140A/B into service while removing from service the heat exchanger that is fouled or otherwise in need of service or maintenance.

In embodiments, at least one heat exchanger is configured to produce low pressure steam. In embodiments, first heat exchanger 140A and second heat exchanger 140B are substantially identical. In embodiments, such as that of FIG. 1, first heat exchanger 140A and second heat exchanger 140B are substantially the same size. Hydrocarbon feed line 105 is fluidly connected with hydrogenation reactor 120, and configured for the introduction of hydrocarbon feed thereto. A hydrogen feed line 115 is fluidly connected with hydrogenation reactor 120, and configured for the introduction of gas containing hydrogen thereto. Reactor liquid phase outlet line 125 fluidly connects hydrogenation reactor 120 with pump 130, whereby a portion of the reactor liquid withdrawn from the liquid phase within hydrogenation reactor 120 can be introduced into pump 130. Pump 130 is fluidly connected with first heat exchanger 140A via pump outlet line 135A, and with second heat exchanger 140B via pump outlet line 135B. Heat exchangers 140A/140B are configured to reduce the temperature of the reactor liquid introduced thereto, via heat exchange with a heat exchange fluid in heat transfer line 145A/145B, respectively. First heat exchanger outlet line 150A fluidly connects first heat exchanger 140A with hydrogenation reactor 120 via recycle line 165, whereby a cooled withdrawn portion of the liquid phase can be reintroduced into hydrogenation reactor 120; second heat exchanger outlet line 150B fluidly connects second heat exchanger 140B with hydrogenation reactor 120 via recycle line 165, whereby cooled withdrawn liquid phase can be reintroduced into hydrogenation reactor 120. A gas phase hydrogenation product outlet line 155 is fluidly connected with hydrogenation reactor 120, and configured for the removal of gas phase hydrogenation product therefrom. A fresh catalyst inlet line 160 is configured to introduce catalyst into hydrogenation reactor 120, for example, via recycle line 165. Valves V1 and V2 are operable to direct flow within the pump-around loop to first heat exchanger 140A or second heat exchanger 140B, respectively.

In embodiments, the first heat exchanger and the second heat exchanger are substantially the same size and operate with the same cooling medium (e.g., boiler feed water for production of low pressure steam) in respective heat transfer lines thereof, and/or operate with cooling media having the same inlet temperatures.

In embodiments, the first heat exchanger and the second heat exchanger are substantially the same size, but operate with a different cooling medium (e.g., boiler feed water for production of low pressure steam in contrast to cooled or chilled water, for example from an ambient evaporative cooling tower) in respective heat transfer lines thereof, and/or operate with cooling media having differing inlet temperatures.

Figure 2:
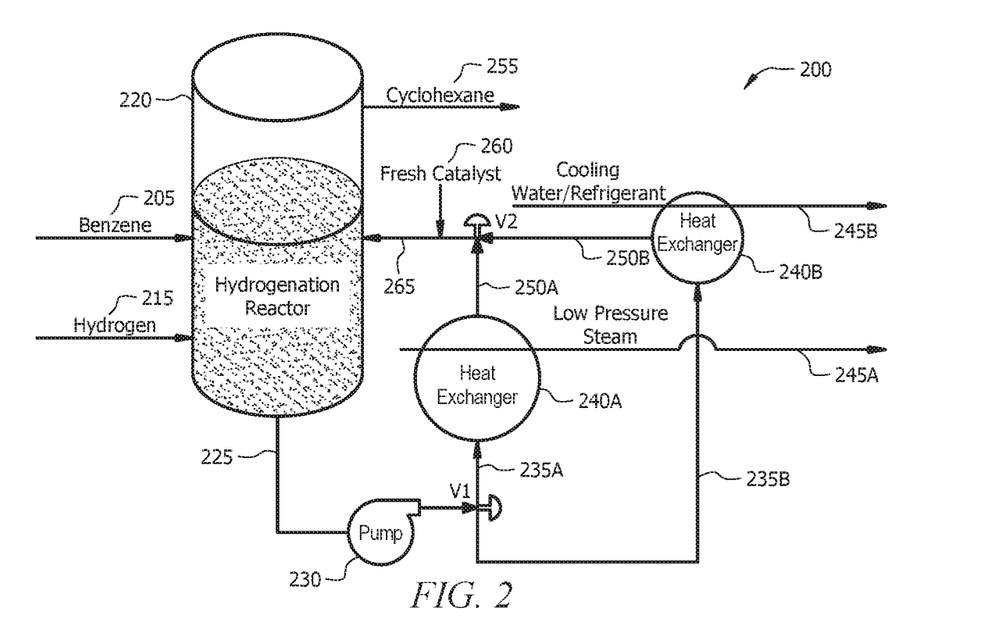
FIG. 2 is a schematic of a liquid phase hydrogenation system which utilizes two disparate heat exchangers, according to another embodiment of this disclosure.

In embodiments, the first heat exchanger and the second heat exchanger are of different sizes. Such an embodiment is depicted in FIG. 2, which is a schematic of a hydrogenation system 200, according to another embodiment of this disclosure which utilizes two heat exchangers, one of which is a smaller swing heat exchanger operable with a different cooling medium than that with which the other heat exchanger operates. In this embodiment, first heat exchanger 240A is larger than second or 'additional' heat exchanger 240B, and first heat exchanger 240A is a primary heat exchanger that is utilized except in situations where same needs cleaning or maintenance. In embodiments, second heat exchanger 240B is a smaller 'swing' heat exchanger, which may allow for capital savings. In such embodiments, the heat throughput of second heat exchanger 240B may be increased and/or the reaction rate decreased, which may be acceptable providing the time needed to clean or otherwise service the primary heat exchanger is sufficiently brief. The heat throughput of second heat exchanger 240B may be increased via utilization of a different cooling medium therein, such as, without limitation, cooling water or refrigerant in contrast to water (e.g., boiler feed water) yielding low pressure steam. In this manner, second heat exchanger 240B may be operable to cool the reactor liquid introduced thereto to a greater extent, thus enabling substantially equivalent heat removal as provided by first heat exchanger 240A, with a lower flow rate. Thus, in embodiments, heat transfer line 245B introduces cooling water or refrigerant into second heat exchanger 240B. In embodiments, primary heat exchanger 240A is configured to produce low pressure steam in heat transfer line 245A. Thus, in embodiments, heat transfer line 245A introduces boiler feed water into and removes low pressure steam from first heat exchanger 240A. In such embodiments, utilization of a smaller 'swing' heat exchanger as second heat exchanger 240B may not enable the production of low pressure steam generation while primary heat exchanger 240A is being serviced.

Figure 1:
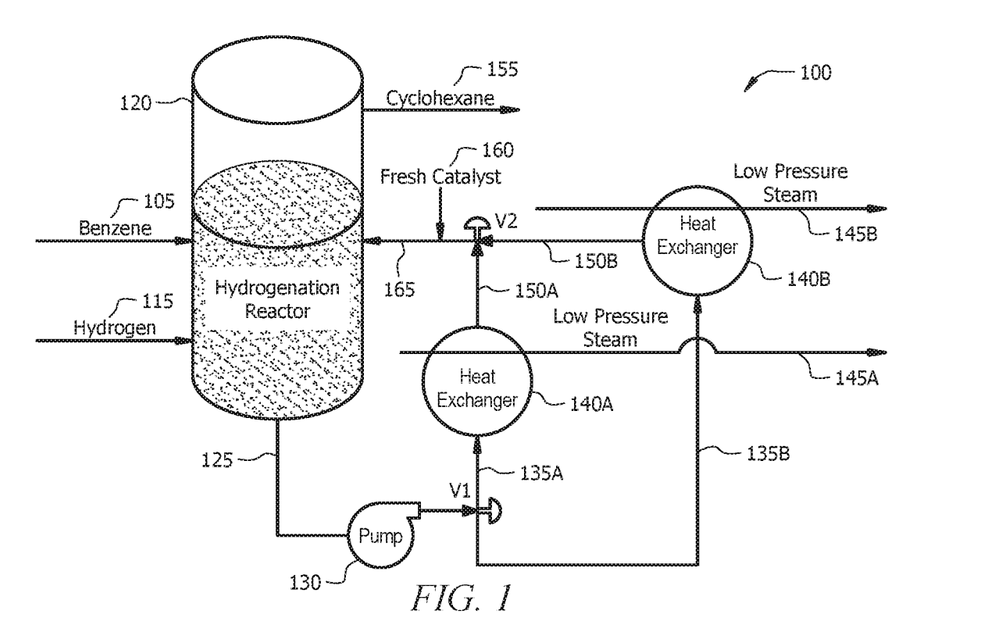
FIG. 1 is a schematic of a liquid phase hydrogenation system which utilizes two substantially equivalent heat exchangers, according to an embodiment of this disclosure.

System 200 comprises hydrogenation reactor 220, pump 230, hydrocarbon feed line 205, hydrogen feed line 215, reactor liquid phase outlet line 225, gas phase hydrogenation product outlet line 255, pump outlet lines 235A and 235B, first heat exchanger outlet line 250A and second heat exchanger outlet line 250B, fresh catalyst inlet line 260, and recycle line 265, which correspond with hydrogenation reactor 120, pump 130, hydrocarbon feed line 105, hydrogen feed line 115, reactor liquid phase outlet line 125, gas phase hydrogenation product outlet line 155, pump outlet lines 135A and 135B, first heat exchanger outlet line 150A and second heat exchanger outlet line 150B, fresh catalyst inlet line 160, and recycle line 165 of the embodiment of FIG. 1.

As noted hereinabove, in embodiments, a hydrogenation system according to this disclosure comprises (b) a separator upstream of the at least one primary heat exchanger, and configured to separate hydrogenation catalyst, a decomposition product of the hydrogenation catalyst, or both, from the withdrawn portion of the reactor liquid phase. Description of such a hydrogenation system will now be made with reference to FIG. 3, which is a schematic of a hydrogenation system, according to another embodiment of this disclosure, which utilizes removal of catalyst upstream of the heat exchange to enhance run length. Hydrogenation system 300 comprises hydrogenation reactor 320, pump 330, separator 370, and heat exchanger 340. Hydrogenation system 300 is operable such that the heat exchanger 340 is not exposed to the hydrogenation catalyst and/or solid decomposition products thereof (or such exposure is reduced/minimized), which thus prevents (or at least reduces/minimizes) plating out and/or accumulation of catalyst component(s) (e.g., nickel) and/or decomposition products thereof (e.g., nickel deposits) on the heat exchanger surfaces. In some such embodiments, the catalyst is supported, and the hydrogenation reaction carried out as a slurry phase.

Figure 3:
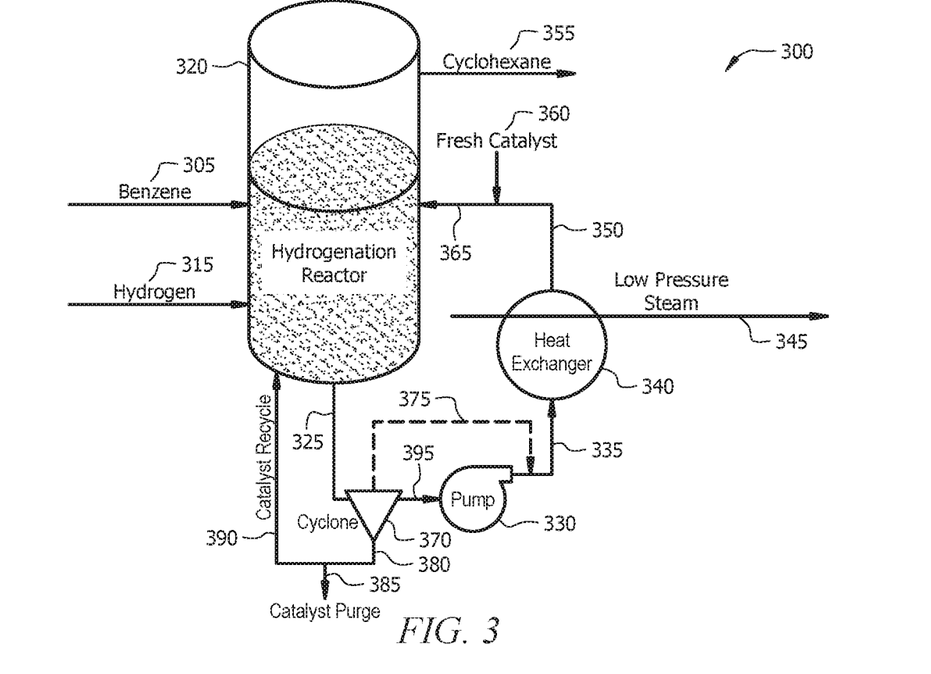
FIG. 3 is a schematic of a liquid phase hydrogenation system which utilizes removal of catalyst, according to another embodiment of this disclosure.

Hydrogenation system 300 comprises reactor liquid phase outlet line 325, which is operable to withdraw reactor liquid from the liquid phase within hydrogenation reactor 320. In embodiments, reactor liquid phase outlet line 325 fluidly connects hydrogenation reactor 320 with separator 370, whereby reactor liquid withdrawn via reactor liquid phase outlet line 325 is introduced into separator 370. Separator 370 may be any separator operable for solid/liquid separation, whereby solid catalyst and/or solid catalyst decomposition product(s) (collectively, "solids") may be separated from the reactor liquid phase introduced thereto. In embodiments, separator 370 comprises a solid/liquid separation device selected from cyclones, filters, gravitational settling chambers, and combinations thereof. In embodiments, separator 370 is operable for on-stream cleaning. In other embodiments, a separator 370, such as, for example, a spent catalyst drum, is operable for off-stream separation of spent catalyst. In embodiments, separator 370 comprises a centrifugal force separator such as a cyclone. A separator liquid outlet line 395 may fluidly connect separator 370 with pump 330, which is configured to pump reactor liquid from which solids have been removed into heat exchanger 340, via pump outlet line 335. A separator solids outlet line 380 is configured for the removal of solids from separator 370. A solids return line 390 may be configured to reintroduce solids separated from the withdrawn reactor liquid phase back into hydrogenation reactor 320. In embodiments, a purge line 385 is configured to remove a portion of the separated solid particles (e.g., solid catalyst particles and/or solid catalyst decomposition product(s)) from system 300. Such purge may be utilized, in embodiments, to maintain a desired catalyst inventory within hydrogenation reactor 320 by, for example, balancing catalyst purge via purge line 385 and introduction of fresh catalyst via fresh catalyst inlet line 360. In this manner, catalyst buildup in system 300 can be avoided.

As noted by dashed line 375 in FIG. 3, separator 370 may, in embodiments, be positioned downstream of pump 330. Thus, separator 370 may be located either upstream or downstream of pump 330.

As noted hereinabove, in embodiments in which run length is increased via separation/removal of solids upstream of a heat exchanger of the pump-around loop, the catalyst can be a supported catalyst. In such embodiments, the catalyst support may be any hydrogenation catalyst support known to those of skill in the art. For example, in embodiments, the catalyst comprises a support selected from silica, alumina, carbon, and combinations thereof.

Hydrocarbon feed line 305 is fluidly connected with hydrogenation reactor 320, and configured for the introduction of hydrocarbon feed comprising an aromatic hydrocarbon to be hydrogenated thereto. A hydrogen feed line 315 is fluidly connected with hydrogenation reactor 320, and configured for the introduction of gas containing hydrogen thereto. As discussed in detail above, reactor liquid phase outlet line 325 fluidly connects hydrogenation reactor 320 with pump 330 or separator 370 (depending on whether separator 370 is positioned upstream or downstream of pump 330), whereby reactor liquid phase withdrawn from hydrogenation reactor 320 can be introduced into pump 330 or separator 370. Pump 330 or separator 370 is fluidly connected with heat exchanger 340 via pump outlet line 335 or separator liquid outlet line 395. Heat exchanger 340 is configured to reduce the temperature of the reactor liquid phase introduced thereto, via heat exchange with a heat exchange fluid in heat transfer line 345. Heat exchanger outlet line 350 fluidly connects heat exchanger 340 with hydrogenation reactor 320 via recycle line 365, whereby cooled reactor liquid phase can be reintroduced into hydrogenation reactor 320. A gas phase hydrogenation product outlet line 355 is fluidly connected with hydrogenation reactor 320, and configured for the removal of gaseous hydrogenation product therefrom. A fresh catalyst inlet line 360 is configured to introduce catalyst into hydrogenation reactor 320, for example, via heat exchanger recycle line 365.

As noted hereinabove, in embodiments, a hydrogenation system according to this disclosure comprises apparatus configured for reducing exposure of the hydrogenation catalyst to oxygen-containing species. Such apparatus may comprise (i) a dryer operable to dry the hydrocarbon feed, the hydrogen feed, or both (i.e., to dry the hydrocarbon feed and the hydrogen feed separately, or dry a mixed feed containing the hydrocarbon feed and the hydrogen feed); (ii) a source of a component that will react with oxygen-containing species in the hydrocarbon feed, the hydrogen feed, or both; or (iii) both a dryer and a source of the component that will react with oxygen-containing species. In embodiments, a hydrogenation system of this disclosure comprises a dryer configured to dry the hydrocarbon feed, the hydrogen feed, both the hydrocarbon feed and the hydrogen, or a combined or mixed feed stream comprising the hydrocarbon feed and the hydrogen feed.

Description of a hydrogenation system comprising apparatus configured for reducing exposure of the hydrogenation catalyst to reactive (e.g., oxygen-containing) species will now be made with reference to FIG. 4, which is a schematic of a hydrogenation system 400, according to another embodiment of this disclosure, which utilizes addition of a component from a source of the component to enhance run length. Hydrogenation system 400 comprises hydrogenation reactor 420, pump 430, and heat exchanger 440. Hydrogenation system 400 is operable such that the level of oxygen-containing species (e.g., carbon monoxide, carbon dioxide, oxygen, water, and the like), in the hydrocarbon feed introduced via hydrocarbon feed line 405 and/or in hydrogen feed introduced via hydrogen feed line 415 is reduced. Reduction of such oxygen-containing species is desirable, as the presence of such species encourages the plating out of catalyst component(s) (e.g., nickel) on the heat exchanger surfaces. In embodiments, a hydrogenation system of this disclosure comprises a dryer 475 configured to dry the hydrocarbon feed, the hydrogen feed, or both (separately, or combined), whereby the level of oxygen-containing species (e.g., water) can be reduced. In embodiments, such a dryer is utilized in conjunction with a source of a component that will react with oxygen-containing species in the hydrocarbon feed, the hydrogen feed, or both. Selectively removing such oxygen-containing species from the reactor or reactor feed(s) may thus provide for enhanced run length, by reducing or preventing plating out of catalyst component(s) and/or decomposition products on the surfaces of the heat exchanger(s).

Figure 4:
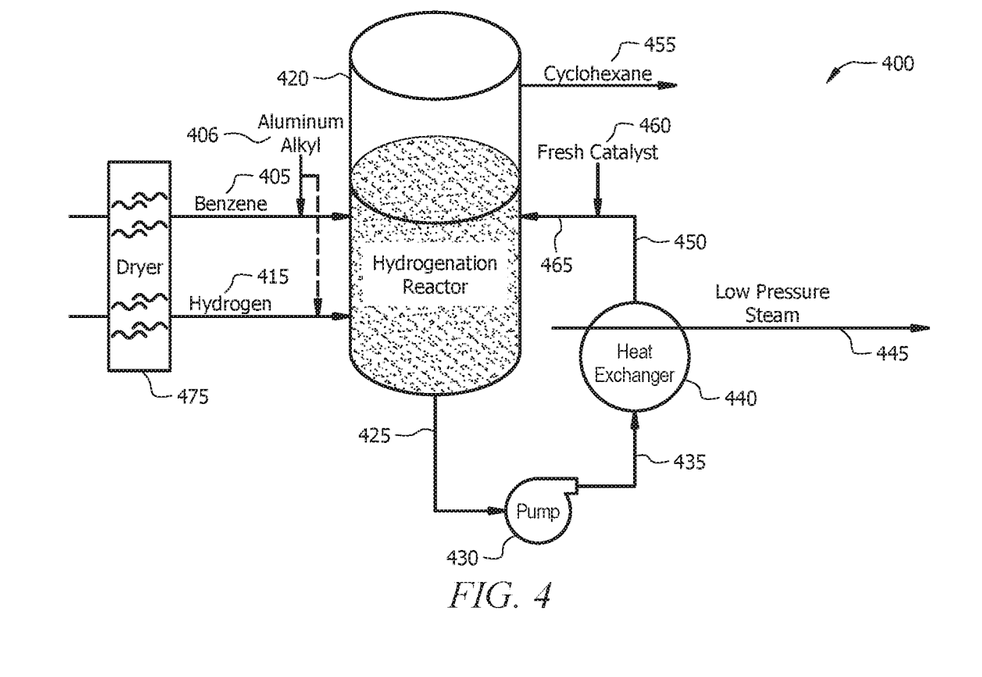
FIG. 4 is a schematic of a liquid phase hydrogenation system which utilizes addition of aluminum alkyls, according to another embodiment of this disclosure.

In the embodiment of FIG. 4, hydrogenation system 400 comprises a source of a component that will react with oxygen-containing species in the hydrocarbon feed, the hydrogen feed, or both. The source of the component comprises component feed line 406, which is configured to introduce a component that will react with oxygen-containing species into hydrocarbon feed line 405. In embodiments, the source of the component (e.g., component feed line 406) is fluidly connected with hydrogen feed line 415, whereby the component that will react with oxygen-containing species is introduced into the hydrogen feed. In embodiments, one or more source of the component (e.g., component feed line 406) is fluidly connected with (a) hydrogen feed line 415, whereby the component that will react with oxygen-containing species is introduced into the hydrogen feed, and (b) with hydrocarbon feed line 405, whereby the component that will react with oxygen-containing species can also be introduced into the hydrocarbon feed. In embodiments, hydrogenation system 400 comprises piping whereby the hydrocarbon feed and the hydrogen feed can be combined to provide a combined or mixed feed prior to introduction of the combined or mixed feed into hydrogenation reactor 420. Such a system may further comprise piping whereby the component that will react with oxygen-containing species can be added via the source of the component (e.g., component feed line 406) to the combined feed.

Desirably, the component that will react with oxygen-containing species added via the source of said component is a species that will quickly react with the oxygen-containing impurities, thus preventing or minimizing detrimental effects such species could have on the hydrogenation catalyst, and/or downstream equipment (e.g., the heat exchanger(s) of the pump-around loop). In embodiments, the component that will react with oxygen-containing species is selected from the group consisting of aluminum alkyls. The aluminum alkyl compound used with the present disclosure can have the formula: $(R^3)_3Al$; in which $(R^3)$ is an aliphatic group having from 1 to about 6 carbon atoms. In some instances, $(R^3)$ is methyl, ethyl, propyl, butyl, hexyl, or isobutyl. In embodiments, the aluminum alkyl compound comprises an aluminum alkyl halide such as, but not limited to, diethylaluminum chloride (DEAC) or dimethylaluminum chloride (DMAC). Utilization of aluminum alkyls as the component that will react with oxygen-containing species may be particularly desirable in systems utilizing catalyst systems that comprise one or more aluminum alkyls, as addition of same would not be expected to undesirably influence the overall reaction. In embodiments, the component that will react with oxygen-containing species is added at a molar ratio of aluminum alkyl to oxygen containing species of between 1:3 and 3:1. In another embodiment, the specific amount can depend on the amount of oxygen and moisture in the feed.

Hydrogenation system 400 further comprises reactor liquid phase outlet line 425, which is operable to withdraw reactor liquid phase from hydrogenation reactor 420. Reactor liquid phase outlet line 425 fluidly connects hydrogenation reactor 420 with pump 430, which is configured to pump reactor liquid into heat exchanger 440, via pump outlet line 435. Hydrocarbon feed line 405 is fluidly connected with hydrogenation reactor 420, and configured for the introduction of hydrocarbon feed thereto. A hydrogen feed line 415 is fluidly connected with hydrogenation reactor 420, and configured for the introduction of gas containing hydrogen thereto. Reactor liquid phase outlet line 425 fluidly connects hydrogenation reactor 420 with pump 430, whereby reactor liquid phase withdrawn from hydrogenation reactor 420 can be introduced into pump 430. Pump 430 is fluidly connected with heat exchanger 440 via pump outlet line 435. Heat exchanger 440 is configured to reduce the temperature of the reactor liquid introduced thereto, via heat exchange with a heat exchange fluid in heat transfer line 445. Heat exchanger outlet line 450 fluidly connects heat exchanger 440 with hydrogenation reactor 420 via recycle line 465, whereby cooled withdrawn reactor liquid phase can be reintroduced into hydrogenation reactor 420. A gas phase hydrogenation product outlet line 455 is fluidly connected with hydrogenation reactor 420, and configured for the removal of gaseous hydrogenation product therefrom. A fresh catalyst inlet line 460 is configured to introduce catalyst into hydrogenation reactor 420, for example, via heat exchanger recycle line 465.

The hydrogenation catalyst introduced via line(s) 160/260/360/460 is any hydrogenation catalyst known to those of skill in the art to be operable to catalyze the desired hydrogenation reaction. In embodiments, the hydrogenation catalyst is a catalyst operable to catalyze the liquid phase hydrogenation of benzene to produce cyclohexane. Such catalyst may be a catalyst known to those of skill in the art. In embodiments, the hydrogenation catalyst comprises soluble and/or colloidal nickel species and aluminum alkyls. In embodiments, the catalyst comprises trialkylaluminum, nickel carboxylate, and sodium carboxylate in a saturated hydrocarbon solution, as described, for example, in U.S. Pat. No. 5,668,293, the disclosure of which is hereby incorporated herein for purposes not contrary to this disclosure.

In embodiments, the catalyst comprises a metal from Group VIII of the periodic table. In embodiments, the catalyst comprises nickel, platinum, palladium, iron, or a combination thereof. In embodiments, the catalyst comprises nickel. In embodiments, the hydrogenation catalyst comprises soluble nickel species and one or more aluminum alkyls. In embodiments, the hydrogenation catalyst comprises a trialkylaluminum, nickel carboxylate, and sodium carboxylate in a saturated hydrocarbon solution as described, for example, in U.S. Pat. No. 5,668,293. In embodiments, a homogeneous or soluble hydrogenation catalyst is employed. In embodiments, the catalyst comprises a solid support. In embodiments, the catalyst support is selected from silica, alumina, magnesia, carbon, and combinations thereof.

Hydrogenation reactor 120/220/320/420 may be any hydrogenation reactor operable for hydrogenation of hydrocarbons with a liquid phase and a gas phase. In embodiments, the hydrogenation reactor is operable with a soluble or homogeneous catalyst. In embodiments, the hydrogenation reactor is operable with a slurry phase of catalyst comprising a catalyst with a solid support. In embodiments, the hydrogenation reactor is not a fixed bed reactor. In embodiments, hydrogenation reactor 120/220/320/420 is a continuous flow reactor with a pump around loop, as described, for example, in U.S. Pat. No. 5,668,293.

In embodiments, the herein-disclosed hydrogenation system further comprises a finishing hydrogenation reactor downstream of hydrogenation reactor 120/220/320/420, and configured to hydrogenate unconverted aromatic hydrocarbon in the gas phase hydrogenation product stream in gas phase hydrogenation product outlet line 155/255/355/455. In embodiments, such a finishing reactor is operable with a solid catalyst. In embodiments, the finishing hydrogenation reactor is operable with a fixed bed of hydrogenation catalyst, as described, for example, in U.S. Pat. No. 5,668,293.

Also disclosed herein is a method for liquid phase hydrogenation of aromatic hydrocarbon(s). The disclosed method provides for hydrogenation of an aromatic hydrocarbon utilizing a hydrogenation reactor operated with a pump-around heat exchanger loop. Run length may be increased via the disclosed method relative to conventional hydrogenation methods, by reducing or eliminating the deposition of hydrogenation catalyst component(s) and/or decomposition products on the surfaces of the heat exchanger and/or enabling heat exchanger cleaning while maintaining operation of the hydrogenation system. Such reduction or elimination of catalyst deposition is provided in a number of ways, including one or more of separating catalyst from the withdrawn reactor fluid upstream of the heat exchanger of the pump-around loop, whereby catalyst does not enter the heat exchanger; removing reactive species from the hydrogenation reactor and/or from the hydrogenation reactor feed(s) (for example, via drying of the feed(s) and/or addition of a component thereto that reacts with said reactive species); utilization of a second heat exchanger in the pump-around loop, such that one heat exchanger may be cleaned and/or serviced while the second heat exchanger is placed online; or combinations thereof.

As noted hereinabove, the disclosed method comprises: introducing a hydrocarbon feed comprising an aromatic hydrocarbon, a hydrogen feed comprising hydrogen, and a hydrogenation catalyst into a hydrogenation reactor operable with a liquid phase and a gas phase, whereby at least a portion of the aromatic hydrocarbon is hydrogenated to produce a hydrogenation product; removing a gas phase product stream comprising the hydrogenation product from the hydrogenation reactor; withdrawing a portion of the reactor liquid phase, subjecting at least a portion of the withdrawn portion of the liquid phase to heat exchange, thus providing a reduced-temperature withdrawn portion, introducing the reduced-temperature withdrawn portion back into the hydrogenation reactor; and at least one of: (a) providing at least two heat exchangers to effect the subjecting of the withdrawn portion of the liquid phase to heat exchange, such that a first heat exchanger of the at least two heat exchangers can be online while a second heat exchanger of the at least two heat exchangers is offline; (b) separating hydrogenation catalyst, a decomposition product of the hydrogenation catalyst, or both, from the withdrawn portion of the liquid phase prior to subjecting the at least a portion of the withdrawn portion of the liquid phase to heat exchange; (c) reducing exposure of the hydrogenation catalyst to an oxygen-containing species; or (d) combinations thereof.

In embodiments, the herein-disclosed hydrogenation method further comprises introducing the gas phase hydrogenation product stream into a finishing hydrogenation reactor downstream of the hydrogenation reactor, whereby unconverted aromatic hydrocarbons in the gas phase hydrogenation product stream are hydrogenated. In embodiments, the finishing reactor is operated with a solid catalyst. In embodiments, the finishing hydrogenation reactor is operated with a fixed bed of hydrogenation catalyst.

Description of the method of this disclosure will now be made with reference to the Figures. FIG. 1 is a schematic of a liquid phase hydrogenation system 100, according to an embodiment of this disclosure, which utilizes two heat exchangers, whereby one can be taken offline for service or maintenance while another is placed online. In this manner, the hydrogenation system can be kept online while a heat exchanger is taken offline.

Hydrocarbon feed and hydrogen feed are introduced via hydrocarbon feed line 105 and hydrogen feed line 115, respectively. The hydrocarbon feed comprises an aromatic hydrocarbon to be hydrogenated. In embodiments, the aromatic hydrocarbon comprises benzene and/or toluene, and the hydrogenation product comprises cyclohexane and/or methyl cyclohexane along with hydrogen feed components. Other minor constituents may be present; for example, a benzene fed may comprise a small amount (e.g., 0.10 wt %) of other C6 components, in embodiments. The hydrogen feed comprises a gas containing hydrogen. In embodiments, the hydrogen feed comprises hydrogen, methane, ethane, propane, n-butane, and isobutene. In embodiments, the hydrogen feed comprises greater than or equal to 90, 95, or 100 volume percent hydrogen. In embodiments, the hydrogen is present in excess of the stoichiometric amount needed to hydrogenate the aromatic hydrocarbon.

Within hydrogenation reactor 120, hydrogenation of the aromatic hydrocarbon is effected in the liquid phase. The operating conditions for carrying out the hydrogenation of aromatic hydrocarbons to naphthenic hydrocarbons are variable and depend mainly on the nature of the hydrocarbon being hydrogenated.

In the case of benzene hydrogenation, the temperature may be in the range of from about 125° C. to about 275° C., from about 170° C. to about 230° C., from about 100° C. to about 200° C., or from about 100° C. to about 250° C. In embodiments, the temperature is low enough (e.g., less than about 250° C.) to prevent hydrocracking of a hydrocarbon feed. The pressure is that pressure sufficient to maintain a liquid phase, and may be in the range of from about 5 to about 100 atmospheres, from about 20 to about 30 atmospheres, or from about 15 to about 30 atmospheres, in embodiments.

As noted hereinabove, the catalyst may be any suitable hydrogenation catalyst known to those of skill in the art. In embodiments, the catalyst comprises a metal from Group VIII of the periodic table. In embodiments, the catalyst comprises nickel. In embodiments, the hydrogenation catalyst comprises soluble nickel species and one or more aluminum alkyls. In embodiments, the hydrogenation catalyst comprises a trialkylaluminum, nickel carboxylate, and sodium carboxylate in a saturated hydrocarbon solution.

As discussed further hereinbelow, in embodiments, the catalyst comprises a solid support, enabling separation of the catalyst from the withdrawn liquid phase prior to heat exchange of a solids-reduced withdrawn portion. In embodiments, the catalyst support is selected from silica, alumina, carbon, and combinations thereof.

Reactor liquid phase is withdrawn from hydrogenation reactor 120 via reactor liquid phase outlet line 125. Pump 130 is operable to pump withdrawn reactor liquid phase from hydrogenation reactor 120 into the pump-around loop, comprising first heat exchanger 140A and second heat exchanger 140B. Withdrawn liquid phase is introduced, via first pump outlet line 135A into first heat exchanger 140A, in which the temperature of the withdrawn reactor liquid phase is reduced via heat exchange with a heat exchange medium passing through first heat exchanger 140A via heat transfer line 145A. In embodiments, first heat exchanger 140A is operable to reduce the temperature of the withdrawn reactor liquid from a temperature by about 5 to 20 degrees Fahrenheit, for example, by about 10° F. (5.5° C.). Reduced-temperature withdrawn liquid phase exiting first heat exchanger 140A via first heat exchanger outlet line 150A is returned to hydrogenation reactor 120 via recycle line 165. To maintain a desired catalyst balance within hydrogenation reactor 120, fresh hydrogenation catalyst can be introduced into hydrogenation reactor 120 via fresh catalyst inlet line 160 and recycle line 165. The catalyst flow rate via fresh catalyst inlet line 160 can be added at a steady rate or in batch mode, and the catalyst injection rate can vary depending on the application, for example between about 1 lb/hr to 500 lb/hr.

Hydrogenation product is recovered from hydrogenation reactor 120. In embodiments, hydrogenation product is removed as a gas from a reactor gas phase, for example via gas phase hydrogenation product outlet line 155. In embodiments, hydrogenation product is removed from hydrogenation reactor 120 as a liquid. In embodiments, hydrogenation product is removed from hydrogenation reactor 120 along with the reactor liquid via reactor liquid phase outlet line 125, and subsequently separated therefrom. In embodiments, the hydrogenation product comprises cyclohexane. In embodiments, the hydrogenation product in reactor liquid phase outlet line 125 comprises from about 20 to about 80, from about 30 to about 70, or from about 30 to about 80 volume percent cyclohexane. In embodiments, the hydrogenation product in line 155 comprises substantially pure (e.g., greater than or equal to about 97, 98, or 99 volume percent) hydrogenation product.

When first heat exchanger 140A is in need of service or repair, valves V1 and V2 are adjusted such that reactor liquid phase withdrawn via reactor liquid phase outlet line 125 is introduced, via second pump outlet line 135B, into second heat exchanger 140B, and bypasses first heat exchanger 140A. In this manner, hydrogenation system 100 can remain online while a heat exchanger is taken offline for cleaning or repair. Within second heat exchanger 140B, the temperature of the withdrawn portion of reactor liquid phase is reduced via heat transfer with a heat transfer medium in heat transfer line 145B. In embodiments, such as the embodiment of FIG. 1, first heat exchanger 140A and second heat exchanger 140B are essentially identical. For example, first and second heat exchangers 140A and 140B may be substantially the same size, may operate with the same heat transfer media, or both. In embodiments, one or both of first heat exchanger 140A and second heat exchanger 140B operate to produce low pressure steam on the shell side thereof, which is obtained therefrom via heat transfer lines 145A and/or 145B. In embodiments, low pressure steam removed via heat transfer line 145A and/or 145B comprises steam having a pressure of less than or equal to about 160 psig (1103 kPag), 140 psig (965 kPag), or 125 psig (861 kPag), and a temperature of less than or equal to about 204° C. (400° F.).

In embodiments, such as that depicted in FIG. 2, which is a schematic of a liquid phase hydrogenation system according to another embodiment of this disclosure, a method of this disclosure may utilize two disparate heat exchangers. The embodiment of FIG. 2 is equivalent to that of FIG. 1, with the exception that, in the embodiment of FIG. 2, hydrogenation system 200 comprises first or 'primary' heat exchanger 240A that is larger than second or 'swing' heat exchanger 240B. In this embodiment, capital savings may be realized by utilizing smaller swing exchanger during times when the primary or first heat exchanger 240A needs service or repair. In such embodiments, the heat throughput of the swing or second heat exchanger can be increased or the hydrogenation reaction rate decreased, such that adequate heat transfer is effected in second or swing heat exchanger 240B. This may be particularly suitable for applications in which cleaning and/or repair of the primary or first heat exchanger takes a sufficiently short amount of time. The first heat exchanger and the second heat exchanger may be operated with cooling media having different compositions, different inlet temperatures, or both. For example, in embodiments, second or swing heat exchanger 240B may be operated with a different cooling medium than that with which first heat exchanger 240A is operated. For example, in embodiments, second or swing heat exchanger 240B is operated with cooling water or refrigerant for the coolant so that the same duty could be achieved with a smaller bundle, while first or primary heat exchanger 240A is operated to produce low pressure steam. In this manner, the heat throughput of secondary or swing heat exchanger 240B can be increased, and the liquid cooled down to a greater extent, thus achieving the same heat removal with a lower flow rate. In this embodiment, low pressure steam generation may be halted while primary heat exchanger 240A is being cleaned.

Description of a method of this disclosure will now be made with reference to FIG. 3, which is a schematic of a liquid phase hydrogenation system 300, according to an embodiment of this disclosure, which utilizes separation of solid catalyst and/or solid catalyst decomposition product(s) from a withdrawn portion of the reactor liquid phase prior to introduction of the withdrawn liquid phase into a heat exchanger of the pump-around loop. In this manner, plating out of catalyst metal(s) and/or of a catalyst decomposition product(s) on and/or within the heat exchanger can be prevented/minimized by preventing/minimizing exposure of the heat exchanger to the hydrogenation catalyst and/or hydrogenation catalyst decomposition product(s).

In the embodiment of FIG. 3, hydrocarbon feed is introduced into hydrogenation reactor 320 via hydrocarbon feed line 305 and hydrogen feed is introduced into hydrogenation reactor 320 via hydrogen feed line 315. Within liquid phase reactor 320, hydrogenation of the aromatic hydrocarbon is carried out at operating conditions as known to those of skill in the art, and briefly outlined hereinabove.

In embodiments, reactor liquid phase comprising a slurry of solid hydrogenation catalyst and/or solid catalyst decomposition product(s) is withdrawn via reactor liquid phase outlet line 325, and introduced into solid/liquid separator 370. Solids (i.e., solid catalyst and/or solid catalyst decomposition product(s)) separated from the withdrawn portion of the liquid phase in separator 370 are removed from separator 370 via separator solid outlet line 380. Separated catalyst can be returned to hydrogenation reactor 320 via solids return line 390. In such embodiments, the hydrogenation catalyst can be a catalyst comprising a solid support. The catalyst support may be any suitable material known to those of skill in the art. In embodiments, the catalyst support comprises silica, alumina, carbon, or a combination thereof. In embodiments, the hydrogenation catalyst comprises nickel and one or more aluminum alkyl species and a support. The catalyst particle size may be such that effective removal is provided in separator 370.

A portion of the separated solids can be purged via purge line 385, whereby a desired level of catalyst can be maintained within hydrogenation reactor 320, and catalyst buildup can be avoided. The amount of catalyst purged via purge line 385 and the amount of fresh catalyst introduced into hydrogenation reactor 320 via fresh catalyst inlet line 360 can be balanced to maintain a desired catalyst inventory within liquid phase hydrogenation system 300. In embodiments, separator 370 is operable to remove solid catalyst decomposition products from the withdrawn portion of the liquid phase, a homogeneous catalyst is utilized, and separated solid decomposition products are removed via purge line 385. In such embodiments, no solids return line 390 is utilized.

Withdrawn reactor liquid phase from which solids have been removed is removed from separator 370 via separator liquid outlet line 395 and pumped via pump 330 and pump outlet line 335 into heat exchanger 340 of the pump-around loop. Within heat exchanger 340, the temperature of the solids-reduced withdrawn reactor liquid phase is reduced, as noted above with reference to the embodiment of FIGS. 1 and 2, via heat exchange with heat transfer medium in heat transfer line 345. Reduced-temperature, solids-reduced withdrawn liquid phase is removed from heat exchanger 340 via heat exchanger outlet line 350, and is reintroduced into hydrogenation reactor 320, (optionally) along with fresh catalyst introduced via fresh catalyst inlet line 360, via recycle line 365.

In alternative embodiments, as indicated via dashed line 375 in FIG. 3, separator 370 is downstream of pump 330. In such embodiments, withdrawn reactor liquid phase in reactor liquid phase outlet line 325 is introduced via pump 330 and pump outlet line 335 into separator 370, and solids-reduced reactor liquid phase removed from separator 370 via separator liquid outlet line 395 is introduced into heat exchanger 340.

Hydrogenation product is removed from reactor 320 as described hereinabove with reference to FIGS. 1 and 2. For example, in embodiments, hydrogenation product is removed from hydrogenation reactor 320 via gas phase hydrogenation product outlet line 355.

In embodiments, a method of this disclosure comprises reducing exposure of the hydrogenation catalyst to reactive species which encourage deposit of catalyst metal on the heat exchanger of the pump-around loop. In embodiments, reducing exposure of the hydrogenation catalyst to oxygen-containing species (e.g., $H_2O$) comprises drying the hydrocarbon feed, the hydrogen feed, both the hydrocarbon feed and the hydrogen feed, or a mixed feed containing both the hydrocarbon feed and the hydrogen feed, prior to introducing same into the hydrogenation reactor, for example with dryer 475 of FIG. 4. In embodiments, reducing exposure of the hydrogenation catalyst to oxygen-containing species comprises adding a component to the hydrocarbon feed, the hydrogen feed, both the hydrocarbon feed and the hydrogen feed, or a mixture of the hydrocarbon feed and the hydrogen feed, wherein the component is a compound that will react with the oxygen-containing species. The compound can be selected from the group consisting of aluminum alkyls. In embodiments, the method comprises combining the hydrocarbon feed and the hydrogen feed to provide a combined feed prior to introducing the combined feed into the hydrogenation reactor. In such embodiments, adding a component to the hydrocarbon feed, the hydrogen feed, or both, comprises adding the component to the combined feed.

Description of such a method of this disclosure will now be made with reference to FIG. 4, which is a schematic of a liquid phase hydrogenation system 400, according to an embodiment of this disclosure, which utilizes addition of a component which reacts with reactive species and thus minimizes or prevents plating out of catalyst metal and/or other catalyst decomposition product(s) on surfaces of the heat exchanger of the pump-around loop. In this manner, plating out of catalyst metal/catalyst decomposition product(s) on the heat exchanger can be prevented/minimized by preventing/minimizing exposure of the heat exchanger to reactive species (such as oxygen-containing species, including but not limited to oxygen, water, carbon monoxide, and carbon dioxide), which encourage the plating out of catalyst metal/catalyst decomposition product(s) on heat exchanger surfaces.

Hydrocarbon feed is introduced into hydrogenation reactor 420 via hydrocarbon feed line 405, and hydrogen is introduced into hydrogenation reactor 420 via hydrogen feed line 415. A component that will quickly react with species that undesirably encourage plating out of catalyst metal (e.g., nickel) and/or catalyst decomposition product(s) on the surfaces within heat exchanger 440, is added from a component source 406 into hydrocarbon feed line 405. In alternative embodiments, the component is added from source 406 into hydrogen feed line 415. In alternative embodiments, the component is added from source 406 into hydrocarbon feed line 405 and hydrogen feed line 415. In alternative embodiments, hydrocarbon feed and hydrogen feed are combined prior to introduction into hydrogenation reactor 420. In such embodiments, the source of the component 406 is configured and the method operated such that the component can be introduced into the combined hydrocarbon/hydrogen feed line prior to introduction into hydrogenation reactor 420. In embodiments, the source of the component is configured and the method operated such that the component can be introduced directly into hydrogenation reactor 420.

The component added to the reactor feed or the hydrogenation reactor to reduce plating out of catalyst metal(s) and/or catalyst decomposition product(s) on the surfaces of heat exchanger 440 of the pump-around loop may comprise any species known to those of skill in the art to quickly react with impurities known to encourage the plating out of catalyst metal/catalyst decomposition product(s) on the surface(s) of heat exchanger 440. In embodiments, the component is a species that quickly reacts with oxygen-containing species, which are known to encourage plating out of catalyst metal(s) on the surfaces of heat exchanger 440. Such component may react with oxygen-containing species, including but not limited to, oxygen, water, carbon monoxide, and carbon dioxide. In embodiments, the component comprises one or more aluminum alkyls. In embodiments, the hydrocarbon comprises benzene, the catalyst comprises soluble nickel species and at least one aluminum alkyl, and the component added to the reactor feed or the reactor comprises one or more aluminum alkyls. In such embodiments, addition of one or more aluminum alkyls to the aromatic hydrocarbon (e.g., benzene) feed, the hydrogen feed, or both, can remove or reduce the levels of oxygen-containing species, thus preventing the detrimental effects such oxygen-containing species may have on the catalyst (e.g., on a nickel catalyst) and the subsequent plating out of catalyst metal on the surfaces of heat exchanger 440. Utilization of aluminum alkyl(s) as the component that will react with the oxygen-containing species may be particularly suitable in applications wherein the hydrogenation catalyst comprises aluminum alkyl(s), as the introduction of additional aluminum alkyl(s) is not expected to undesirably influence the overall reaction.

In embodiments, the component added to reduce exposure of the hydrogenation catalyst to oxygen-containing species is added at a molar ratio of the component to oxygen-containing species of between 1:3 and 3:1. In another embodiment, the specific amount can depend on the amount of oxygen and moisture in the feed.

A portion of the reactor liquid phase is withdrawn from hydrogenation reactor 420 via reactor liquid phase outlet line 425, and pumped via pump 430 and pump outlet line 435 into heat exchanger 440 of the pump-around loop. Within heat exchanger 440, the temperature of the withdrawn reactor liquid phase is reduced as noted hereinabove with reference to FIG. 2, via heat exchanger with heat transfer medium in heat transfer line 445. Cooled reactor liquid is removed from heat exchanger 440 via heat exchanger outlet line 450, and introduced into hydrogenation reactor 420 via recycle line 465. Fresh catalyst can be introduced into hydrogenation reactor 420 via fresh catalyst inlet line 460 and recycle line 465. Hydrogenation product is removed from hydrogenation reactor 420 as described hereinabove with reference to FIG. 2. For example, in the embodiment of FIG. 4, gaseous hydrogenation product is removed from hydrogenation reactor 420 via gas phase hydrogenation product outlet line 455.

The system and method of this disclosure provide for increased run length of a hydrogenation reactor and reduction in fouling of a heat exchanger of a pump-around loop. In embodiments, run length is increased by utilization of multiple heat exchangers, such that hydrogenation may be continued while one of the heat exchangers is taken offline for service or repair. In embodiments, fouling of a heat exchanger of the pump-around loop of a hydrogenation system is reduced or prevented by operating the hydrogenation with a supported hydrogenation catalyst in a slurry, and separation of the catalyst from a withdrawn portion of the reactor liquid phase upstream of a heat exchanger of the pump-around loop. In embodiments, fouling of a heat exchanger of the pump-around loop of a hydrogenation system is reduced or prevented by separating solid catalyst decomposition product(s) from a withdrawn portion of the reactor liquid phase upstream of a heat exchanger of the pump-around loop. In embodiments, fouling of a heat exchanger of the pump-around loop of a hydrogenation system is reduced or prevented by removing reactive species, which encourage plating out of catalyst metal(s) on the surfaces of the heat exchanger and/or accumulation of catalyst decomposition product(s) within the heat exchanger of the pump-around loop. Such reactive species may be removed via drying of the reactor feed(s), via the addition of a component that reacts with the reactive species, thus removing them from the system, or both.

The herein-disclosed system and method may enable an extension of the hydrogenation run time before the system is taken offline for service (e.g., for cleaning of a heat exchanger of a pump-around loop), or may eliminate the need for such intervals of non-production altogether. In embodiments, the run time provided via the system and method of this disclosure is increased by at least 10, 20, 30, 40, 50, 60, 70, 80, 90 or 100% relative to a conventional hydrogenation system or method. In embodiments, the run time provided via the system and method of this disclosure is increased by a factor of 2, 2.5, or 3 relative to a conventional hydrogenation system or method. In embodiments, the herein-disclosed system and method reduce catalyst consumption.

It is envisaged that the above-described apparatus and methods may be combined, in certain applications. For example, the addition of a component that reacts with reactive species that promote plating out of catalyst component(s) on the heat exchanger may be utilized in conjunction with multiple heat exchangers, separation of supported hydrogenation catalyst and/or solid catalyst decomposition product(s) upstream of the heat exchanger of the pump-around loop, or any combination thereof.

Additional Disclosure

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Embodiments disclosed herein include:

A: A process for liquid phase hydrogenation of an aromatic hydrocarbon, the process comprising: introducing a hydrocarbon feed comprising the aromatic hydrocarbon, a hydrogen feed comprising hydrogen, and a hydrogenation catalyst into a hydrogenation reactor operable with a liquid phase and a gas phase, whereby at least a portion of the aromatic hydrocarbon is hydrogenated to produce a hydrogenation product; removing, from the hydrogenation reactor, a gas phase product stream comprising the hydrogenation product; withdrawing, from the hydrogenation reactor, a portion of the liquid phase; subjecting at least a portion of the withdrawn portion of the liquid phase to heat exchange, thus providing a reduced-temperature withdrawn portion; introducing the reduced-temperature withdrawn portion back into the hydrogenation reactor; and at least one of: (a) providing at least two heat exchangers to effect the subjecting of the withdrawn portion of the liquid phase to heat exchange, such that a first heat exchanger of the at least two heat exchangers can be online while a second heat exchanger of the at least two heat exchangers is offline; (b) separating a decomposition product of the hydrogenation catalyst, the hydrogenation catalyst, or both, from the withdrawn portion of the liquid phase prior to subjecting the at least a portion of the withdrawn portion of the liquid phase to heat exchange; and (c) reducing exposure of the hydrogenation catalyst to an oxygen-containing species.

B: A process for hydrogenation of benzene to cyclohexane, the process comprising: introducing a benzene feed comprising benzene, a hydrogen feed comprising hydrogen, and a hydrogenation catalyst comprising nickel into a hydrogenation reactor operable with a liquid phase and a gas phase, whereby at least a portion of the benzene is hydrogenated to produce cyclohexane; removing from the hydrogenation reactor a gas phase product stream comprising cyclohexane; withdrawing from the liquid phase a pump-around stream from the reactor; passing at least a portion of the pump-around stream to a heat exchanger bank comprising at least a first heat exchanger in parallel with a second heat exchanger such that the first heat exchanger can be online while the second heat exchanger is offline, and vice versa; cooling the at least a portion of the pump-around stream in the heat exchanger bank to provide a reduced-temperature pump-around stream; and introducing the reduced-temperature pump-around stream back into the hydrogenation reactor.

C: A process for hydrogenation of benzene to cyclohexane, the process comprising: introducing a benzene feed comprising benzene, a hydrogen feed comprising hydrogen, and a hydrogenation catalyst slurry comprising a supported nickel catalyst into a hydrogenation reactor operable with a liquid phase and a gas phase, whereby at least a portion of the benzene is hydrogenated to produce cyclohexane; removing a product stream comprising cyclohexane from the gas phase of the hydrogenation reactor; withdrawing a pump-around stream from the liquid phase of the hydrogenation reactor, wherein the pump-around stream comprises supported nickel catalyst; separating the supported nickel catalyst from the pump-around stream to produce a supported nickel catalyst stream and a substantially catalyst-free pump-around stream; passing at least a portion of the substantially catalyst-free pump-around stream to a heat exchanger; cooling the at least a portion of the substantially catalyst-free pump-around stream in the heat exchanger to provide a reduced-temperature pump-around stream; and introducing the reduced-temperature pump-around stream and at least a portion of the supported nickel catalyst stream back into the hydrogenation reactor.

D: A process for hydrogenation of benzene to cyclohexane, the process comprising: treating a benzene feed comprising benzene to form a treated benzene feed, treating a hydrogen feed comprising hydrogen to form a treated hydrogen feed, both treating a benzene feed comprising benzene to form a treated benzene feed and treating a hydrogen feed comprising hydrogen to form a treated hydrogen feed, or treating a mixed feed comprising benzene and hydrogen to form a treated mixed feed, wherein treating reduces an amount of oxygen-containing species therein, wherein the oxygen containing species comprise carbon monoxide, carbon dioxide, oxygen, water, or a combination thereof; introducing the treated benzene feed, the treated hydrogen feed, both the treated benzene feed and the treated hydrogen feed, or the treated mixed feed, and a hydrogenation catalyst comprising nickel and at least one aluminum alkyl into a hydrogenation reactor operable with a liquid phase and a gas phase, whereby at least a portion of the benzene is hydrogenated to produce cyclohexane; removing a product stream comprising cyclohexane from the gas phase of the hydrogenation reactor; withdrawing a pump-around stream from the liquid phase of the hydrogenation reactor; passing at least a portion of the liquid phase pump-around stream to a heat exchanger; cooling the at least a portion of the liquid phase pump-around stream in the heat exchanger to provide a reduced-temperature pump-around stream, and introducing the reduced-temperature pump-around stream back into the hydrogenation reactor.

E: A system for liquid phase hydrogenation, the system comprising: a hydrogenation reactor operable with a liquid phase and a gas phase to convert an aromatic hydrocarbon in a hydrocarbon feed to a hydrogenation product by contacting the aromatic hydrocarbon with hydrogen in a hydrogen feed in the presence of a hydrogenation catalyst; a pump-around loop comprising a pump configured to move a withdrawn portion of the liquid phase from the hydrogenation reactor through the pump-around loop and back to the hydrogenation reactor; at least one primary heat exchanger after the pump in the pump-around loop and configured to reduce the temperature of at least a portion of the liquid phase withdrawn from the hydrogenation reactor, thus providing a reduced-temperature withdrawn portion, prior to introduction of the reduced-temperature withdrawn portion into the hydrogenation reactor; and at least one of: (a) at least one additional heat exchanger in parallel with the at least one primary heat exchanger, and configured such that the at least one primary heat exchanger can be placed offline while the at least one additional heat exchanger is placed online; (b) a separator upstream of the at least one primary heat exchanger, and configured to separate a decomposition product of the hydrogenation catalyst, the hydrogenation catalyst, or both from the withdrawn portion of the liquid phase; and (c) a dryer operable to dry the hydrocarbon feed, the hydrogen feed, both the hydrocarbon feed and the hydrogen feed, or a mixture of the hydrocarbon feed and the hydrogen feed; a source of a component that will react with an oxygen-containing species in the hydrocarbon feed, the hydrogen feed, or both; or both the dryer and the source of the component.

Each of embodiments A, B, C, D, and E may have one or more of the following additional elements: Element 1: wherein the aromatic hydrocarbon comprises benzene and the hydrogenation product comprises cyclohexane. Element 2: wherein the hydrogenation catalyst comprises nickel, and at least one aluminum alkyl. Element 3: wherein the first heat exchanger and the second heat exchanger are substantially identical, and wherein subjecting the at least a portion of the withdrawn portion of the liquid phase to heat exchange produces a low pressure steam product. Element 4: further comprising operating with one of the at least two heat exchangers offline in order to remove a catalyst decomposition product therefrom. Element 5: wherein the first heat exchanger is larger than the second heat exchanger. Element 6: wherein the first heat exchanger operates with a first cooling medium and the second heat exchanger operates with a second cooling medium, wherein the first cooling medium and the second cooling medium have different compositions, the first heat exchanger and the second heat exchanger have different inlet temperatures, or both. Element 7: further comprising operating with the first heat exchanger offline in order to remove a catalyst decomposition product therefrom. Element 8: wherein the first cooling medium of the first heat exchanger is a boiler feed water stream and a low pressure steam is produced therein, and wherein the second cooling medium is selected from the group consisting of cooling water and refrigerants. Element 9: wherein the hydrogenation catalyst is introduced as a liquid phase catalyst, as a slurry comprising a solid catalyst, or both. Element 10: wherein separating the decomposition product of the hydrogenation catalyst, the hydrogenation catalyst, or both, from the withdrawn portion of the liquid phase comprises passing the withdrawn portion of the liquid phase through a cyclone. Element 11: wherein the at least a portion of the withdrawn portion of the liquid phase is pumped into the at least one heat exchanger via a pump, and wherein the cyclone is downstream of the pump and upstream of the heat exchange, or upstream of the pump. Element 12: wherein the hydrogenation catalyst is introduced as a slurry catalyst. Element 13: wherein separating the decomposition product of the hydrogenation catalyst, the hydrogenation catalyst, or both, from the withdrawn portion of the liquid phase comprises passing the withdrawn portion of the liquid phase through a cyclone. Element 14: further comprising reintroducing at least a portion of the separated hydrogenation catalyst into the hydrogenation reactor. Element 15: further comprising removing at least a portion of the separated decomposition product of the hydrogenation catalyst, at least a portion of the separated hydrogenation catalyst, or both from the process. Element 16: wherein the hydrogenation catalyst further comprises a support. Element 17: wherein the support is selected from the group consisting of silica, alumina, carbon, and combinations thereof. Element 18: wherein reducing exposure of the hydrogenation catalyst to the oxygen-containing species comprises drying the hydrocarbon feed, the hydrogen feed, both the hydrocarbon feed and the hydrogen feed, or a mixture of the hydrocarbon feed and the hydrogen feed prior to introducing same into the hydrogenation reactor. Element 19: wherein reducing exposure of the hydrogenation catalyst to oxygen-containing species comprises contacting the hydrocarbon feed, the hydrogen feed, both the hydrocarbon feed and the hydrogen feed, or a mixture of the hydrocarbon feed and the hydrogen feed, with a component, wherein the component is a compound that will react with the oxygen-containing species. Element 20: wherein the component is selected from the group consisting of aluminum alkyls. Element 21: wherein contacting the hydrocarbon feed, the hydrogen feed, both the hydrocarbon feed and the hydrogen feed, or a mixture of the hydrocarbon feed and the hydrogen feed with the component comprises adding the component to the mixture. Element 22: wherein the component is selected from the group consisting of aluminum alkyls. Element 23: wherein the second heat exchanger is online and the first heat exchanger is offline, and further comprising servicing the first heat exchanger to remove a catalyst decomposition product therefrom. Element 24: wherein the first heat exchanger and the second heat exchanger are about the same size, and wherein the first heat exchanger and the second heat exchanger produce low pressure steam when cooling the at least a portion of the pump-around stream. Element 25: wherein the first heat exchanger and the second heat exchanger are not about the same size, wherein the first heat exchanger is larger and produces low pressure steam when cooling the at least a portion of the pump-around stream, and wherein the second heat exchanger is smaller and is cooled with cooling water or a refrigerated liquid. Element 26: wherein the treating comprises drying. Element 27: wherein the treating comprises the addition of at least one aluminum alkyl. Element 28: wherein the at least one primary heat exchanger is configured to produce low pressure steam. Element 29: wherein the at least one primary heat exchanger and the at least one additional heat exchanger are substantially identical. Element 30: wherein the at least one primary heat exchanger is larger than the at least one additional heat exchanger. Element 31: wherein the separator comprises a cyclone upstream or downstream of the pump. Element 32: wherein the cyclone is downstream of the pump. Element 33: wherein the hydrogenation catalyst further comprises a support. Element 34: wherein the support is selected from the group consisting of silica, alumina, carbon, and combinations thereof. Element 35: further comprising a recycle line whereby at least a portion of the separated hydrogenation catalyst can be reintroduced into the hydrogenation reactor. Element 36: further comprising a line via which at least a portion of the separated hydrogenation catalyst can be purged. Element 37: comprising the dryer. Element 38: comprising the source of the component. Element 39: wherein the component is selected from the group consisting of aluminum alkyls. Element 40: further comprising piping whereby the hydrocarbon feed and the hydrogen feed can be combined to provide a combined feed prior to introduction of the combined feed into the hydrogenation reactor. Element 41: further comprising piping whereby the component can be added from the source of the component to the combined feed.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for liquid phase hydrogenation of an aromatic hydrocarbon, the process comprising:
    introducing a hydrocarbon feed comprising the aromatic hydrocarbon, a hydrogen feed comprising hydrogen, and a hydrogenation catalyst into a hydrogenation reactor operable with a liquid phase and a gas phase, whereby at least a portion of the aromatic hydrocarbon is hydrogenated to produce a hydrogenation product;
    removing, from the hydrogenation reactor, a gas phase product stream comprising the hydrogenation product;
    withdrawing, from the hydrogenation reactor, some portion of the liquid phase, wherein the withdrawn liquid phase comprises a decomposition product of the hydrogenation catalyst, the hydrogenation catalyst, or both;
    subjecting the withdrawn liquid phase to heat exchange, thus providing a reduced-temperature withdrawn liquid phase;
    introducing the reduced-temperature withdrawn liquid phase back into the hydrogenation reactor;
    providing at least two heat exchangers to reduce the temperature of the withdrawn liquid phase via heat exchange, such that a first heat exchanger of the at least two heat exchangers can be online while a second heat exchanger of the at least two heat exchangers is offline; and
    reducing exposure of the hydrogenation catalyst to an oxygen-containing species.

2. The process of claim 1, wherein the aromatic hydrocarbon comprises benzene and the hydrogenation product comprises cyclohexane; wherein the hydrogenation catalyst comprises nickel and at least one aluminum alkyl; or both.

3. The process of claim 1, wherein the hydrogenation catalyst is introduced as a liquid phase catalyst, as a slurry comprising a solid catalyst, or both.

4. The process of claim 3, further comprising separating the decomposition product of the hydrogenation catalyst, the hydrogenation catalyst, or both, from the withdrawn liquid phase prior to subjecting the withdrawn liquid phase to heat exchange, and wherein separating the decomposition product of the hydrogenation catalyst, the hydrogenation catalyst, or both, from the withdrawn liquid phase comprises passing the withdrawn liquid phase through a cyclone.

5. The process of claim 4, wherein the withdrawn liquid phase is pumped into the at least one heat exchanger via a pump, and wherein the cyclone is downstream of the pump and upstream of the heat exchange or upstream of the pump.

6. The process of claim 3, wherein the hydrogenation catalyst is introduced as a slurry catalyst.

7. The process of claim 4 further comprising reintroducing at least a portion of the separated hydrogenation catalyst into the hydrogenation reactor.

8. The process of claim 1, wherein reducing exposure of the hydrogenation catalyst to the oxygen-containing species comprises drying the hydrocarbon feed, the hydrogen feed, both the hydrocarbon feed and the hydrogen feed, or a mixture of the hydrocarbon feed and the hydrogen feed prior to introducing same into the hydrogenation reactor.

9. The process of claim 1, wherein reducing exposure of the hydrogenation catalyst to oxygen-containing species comprises contacting the hydrocarbon feed, the hydrogen feed, both the hydrocarbon feed and the hydrogen feed, or a mixture of the hydrocarbon feed and the hydrogen feed, with a component, wherein the component is a compound that will react with the oxygen-containing species.

10. The process of claim 1, wherein the first heat exchanger and the second heat exchanger are substantially identical, and wherein subjecting the withdrawn liquid phase to heat exchange produces a low pressure steam product.

11. The process of claim 1 further comprising operating with one of the at least two heat exchangers offline in order to remove a catalyst decomposition product therefrom.

12. The process of claim 1, wherein the first heat exchanger is larger than the second heat exchanger.

13. The process of claim 1, wherein the first heat exchanger operates with a first cooling medium and the second heat exchanger operates with a second cooling medium, wherein the first cooling medium and the second cooling medium have different compositions, the first heat exchanger and the second heat exchanger have different inlet temperatures, or both.

14. The process of claim 13 further comprising operating with the first heat exchanger offline in order to remove a catalyst decomposition product therefrom.

15. The process of claim 14, wherein the first cooling medium of the first heat exchanger is a boiler feed water stream and a low pressure steam is produced therein, and wherein the second cooling medium is selected from the group consisting of cooling water and refrigerants.

16. A process for hydrogenation of benzene to cyclohexane, the process comprising:
   introducing a benzene feed comprising benzene, a hydrogen feed comprising hydrogen, and a hydrogenation catalyst comprising nickel into a hydrogenation reactor operable with a liquid phase and a gas phase, whereby at least a portion of the benzene is hydrogenated to produce cyclohexane;
   removing from the hydrogenation reactor a gas phase product stream comprising cyclohexane;
   withdrawing from the liquid phase a pump-around stream from the reactor;
   passing at least a portion of the pump-around stream to a heat exchanger bank comprising at least a first heat exchanger in parallel with a second heat exchanger such that the first heat exchanger can be online while the second heat exchanger is offline, and vice versa;
   cooling the at least a portion of the pump-around stream in the heat exchanger bank to provide a reduced-temperature pump-around stream;
   introducing the reduced-temperature pump-around stream back into the hydrogenation reactor; and
   reducing exposure of the hydrogenation catalyst to an oxygen-containing species.

17. The process of claim 16:
   wherein the first heat exchanger and the second heat exchanger are about the same size, and wherein the first heat exchanger and the second heat exchanger produce low pressure steam when cooling the at least a portion of the pump-around stream; or
   wherein the first heat exchanger and the second heat exchanger are not about the same size, wherein the first heat exchanger is larger and produces low pressure steam when cooling the at least a portion of the pump-around stream, and wherein the second heat exchanger is smaller and is cooled with cooling water or a refrigerated liquid.

18. The process of claim 16, wherein reducing exposure of the hydrogenation catalyst to an oxygen-containing species comprises drying, adding at least one aluminum alkyl, or a combination thereof.

19. The process of claim 16, wherein the second heat exchanger is online and the first heat exchanger is offline, and further comprising servicing the first heat exchanger to remove a catalyst decomposition product therefrom.

20. The process of claim 16:
   wherein the first heat exchanger and the second heat exchanger are about the same size, and wherein the first heat exchanger and the second heat exchanger produce low pressure steam when cooling the at least a portion of the pump-around stream; or
   wherein
   the first heat exchanger and the second heat exchanger are not about the same size, wherein the first heat exchanger is larger and produces low pressure steam when cooling the at least a portion of the pump-around stream, and wherein the second heat exchanger is smaller and is cooled with cooling water or a refrigerated liquid.

21. The process of claim 16, further comprising:
   separating a decomposition product of the hydrogenation catalyst, the hydrogenation catalyst, or both, from the pump-around stream prior to passing the at least a portion of the pump around stream to the heat exchange bank.

* * * * *